United States Patent [19]
Staehlin

[11] Patent Number: 5,636,640
[45] Date of Patent: Jun. 10, 1997

[54] LIQUID SAMPLING AND TEST APPARATUS

[75] Inventor: John H. Staehlin, Lutherville, Md.

[73] Assignee: Volunteers for Medical Engineering, Baltimore, Md.

[21] Appl. No.: 384,657

[22] Filed: Feb. 6, 1995

[51] Int. Cl.$^6$ .................................................. A61B 5/00
[52] U.S. Cl. .................................. 128/764; 604/201
[58] Field of Search .................................. 128/760, 763, 128/764; 604/90, 201, 176, 134

[56] References Cited

U.S. PATENT DOCUMENTS

| | | | |
|---|---|---|---|
| 3,782,377 | 1/1974 | Rychlik | 128/132 |
| 3,872,730 | 3/1975 | Ringrose et al. | 73/869.23 |
| 4,326,541 | 4/1982 | Eckels | 128/760 |
| 4,361,149 | 11/1982 | Wörder | 128/215 |
| 4,639,250 | 1/1987 | Rycroft | 604/201 |
| 4,703,761 | 11/1987 | Rathbone et al. | 128/763 |
| 4,747,829 | 5/1988 | Jacob et al. | 604/110 |
| 4,774,964 | 10/1988 | Bonaldo | 128/763 |
| 4,781,700 | 11/1988 | Vicario | 604/234 |
| 4,804,371 | 2/1989 | Vaillancourt | 604/198 |
| 4,863,453 | 9/1989 | Berger et al. | 604/415 |
| 4,865,592 | 9/1989 | Rycroft | 604/197 |
| 4,883,068 | 11/1989 | Dechow | 128/760 |
| 5,014,718 | 5/1991 | Mitchen | 128/771 |
| 5,064,411 | 11/1991 | Gordon, III | 604/48 |
| 5,122,117 | 6/1992 | Haber et al. | 604/90 |
| 5,167,641 | 12/1992 | Schmitz | 604/196 |
| 5,505,212 | 4/1996 | Keljmann et al. | 128/760 |

FOREIGN PATENT DOCUMENTS

| 2098486 | 5/1981 | United Kingdom | 606/182 |
|---|---|---|---|

*Primary Examiner*—Sam Rimell
*Assistant Examiner*—Pamela L. Wingood
*Attorney, Agent, or Firm*—Finnegan, Henderson, Farabow, Garrett & Dunner

[57] ABSTRACT

An apparatus for sampling blood which includes a deformable housing defining a chamber that retains liquid. The housing has a pierceable membrane. The apparatus also includes a resilient piercer member that is adjacent the wall of a chamber and adapted to puncture the pierceable membrane. A removable layer that covers at least a portion of the pierceable membrane. Depression of the deformable housing proximate the piercer member urges the piercer member to puncture the pierceable membrane. The piercer member thereby forms an opening, allowing liquid to be drawn through the opening and into the chamber. Thereafter, the piercer member returns into the deformable housing.

17 Claims, 14 Drawing Sheets

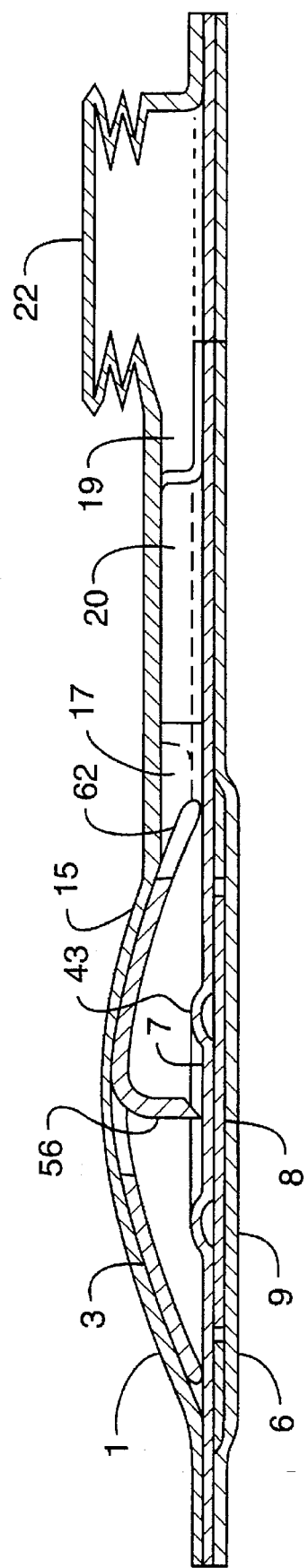

LIQUID SAMPLING AND TEST APPARATUS

BACKGROUND OF THE INVENTION

1. Field of the Invention

This invention relates to apparatus for sampling and testing liquid, such as blood.

2. Description of the Prior Art

There are numerous systems for extracting and testing blood, including U.S. Pat. Nos. 5,167,641, 5,122,117, 4,883,068 and 4,363,453. These systems generally are complicated to assemble or cumbersome to operate.

SUMMARY OF THE INVENTION

It is an object of the present invention to provide apparatus and methods for overcoming the drawbacks of the prior art.

More specifically, it is an object of the present invention to provide apparatus and methods for sampling and testing liquid, such as blood, in a single step with a totally evacuated sealed sterile assembly.

It is also object of the present invention to provide apparatus and method for using a housing which upon coagulation of a sample of blood is rendered unusable.

It is another object of the present invention to provide a low cost, safe and easy to use blood sampling apparatus for individuals and clinical personnel.

It is another object of the present invention to provide an improved blood sampling apparatus where an element for piercing is totally enclosed within a sterile evacuatable cavity, which accumulates blood. This piercing element fits closely into the housing of the evacuatable cavity or chamber, thereby forming an integral unit. The actuation of the piercer consists of a single action of depressing the dome shaped head of the piercer, which action simultaneously adheres the sealing ring of the device to the epidermis, moves the piercer to pierce the pierceable membrane, and then punctures the epidermis. Once the blood fills the evacuatable cavity the piercer then retracts to its original position when the pressure on the dome shaped head is released, thereby eliminating the risk of inadvertent pricking.

It is another object of this device to provide a substantially non-pierceable disk on a protective cover aligned with the piercer. This disk adheres to the sealing ring ensuring that no one will be inadvertently pricked by an accidental depression of the piercer.

It is another object to provide a blood sampling apparatus for use in the blood coagulation time measurement where the sampler assembly has integral electrical contacts which, when connected to appropriate electronic circuitry, automatically trigger the timing sequence by measuring of the presence of blood within the chamber of the blood sampling apparatus.

It is another object to provide a window area and a fiber optic guide means for the infrared energy from an infrared source up to through the blood and out from the opposite side of the blood sample to an infrared detector, so that a remote processor can be used to provide real time accurate blood coagulation time measurement.

It is another object to provide a blood sampling apparatus with integral reagents which, when dissolved into the blood sample, establish the level of the particular property of the blood for which the test was taken.

Other objects and advantages of the present invention will become apparent from the following detailed description when viewed with the accompanying drawings.

To achieve these and other advantages, the present invention comprises a deformable housing defining a cavity adapted to retain a liquid, the housing having a pierceable membrane. The apparatus also comprises a piercer member and a removable layer covering at least a portion of the pierceable membrane. The piercer member, or simply piercer, is integrally formed along said housing and adapted to puncture said pierceable membrane. According to the present invention, depression of the housing proximate said pierceable member punctures said membrane to form an opening and engage the object, so that liquid is drawn from the object through said opening and into the cavity.

Preferably, the apparatus of the present invention includes a seal member attached to a portion of the pierceable membrane for applying a seal between the housing and the object being tested, that is, once the layer is removed.

According to preferred embodiment of the present invention, the apparatus for sampling liquid is used to draw blood from an individual for testing. The blood sampling apparatus includes a protective cover that provides a sterile closure for an adhesive strip sealing. The cover is a non-pierceable disk, which prevents anyone from being pricked inadvertently by the piercer in the main body's evacuatable cavity. The peeled back protective cover is designed to remain on the main body of the apparatus, so that after extracting the blood sample it can be reattached to the main body, thereby eliminating the risk of inadvertent pricking during the time the blood within the previously evacuatable cavity is coagulating. Once the blood within the cavity coagulates, then the dome-like cover is rendered incapable of inadvertent deflection, and the piercer is therefore safely stored within the coagulated blood-filled evacuatable cavity.

In a preferred embodiment of the blood sampler device, the mixing material is in the form of a dry coating within the blood sampling apparatus chamber into which the blood being extracted enters. In another embodiment the mixing material is enclosed within a frangible annulus that is inside the evacuatable cavity. The annulus is broken when the dome is depressed to pierce the pierceable membrane. This allows the incoming blood to mix with the mixing material previously contained in the frangible annulus.

BRIEF DESCRIPTION OF THE DRAWINGS

FIGS. 6a and 6b each show a side view of the apparatus where the blood filling action is enhanced by incorporating a bellows-like syringe at the termination of the filling circuit.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

Figure 1:
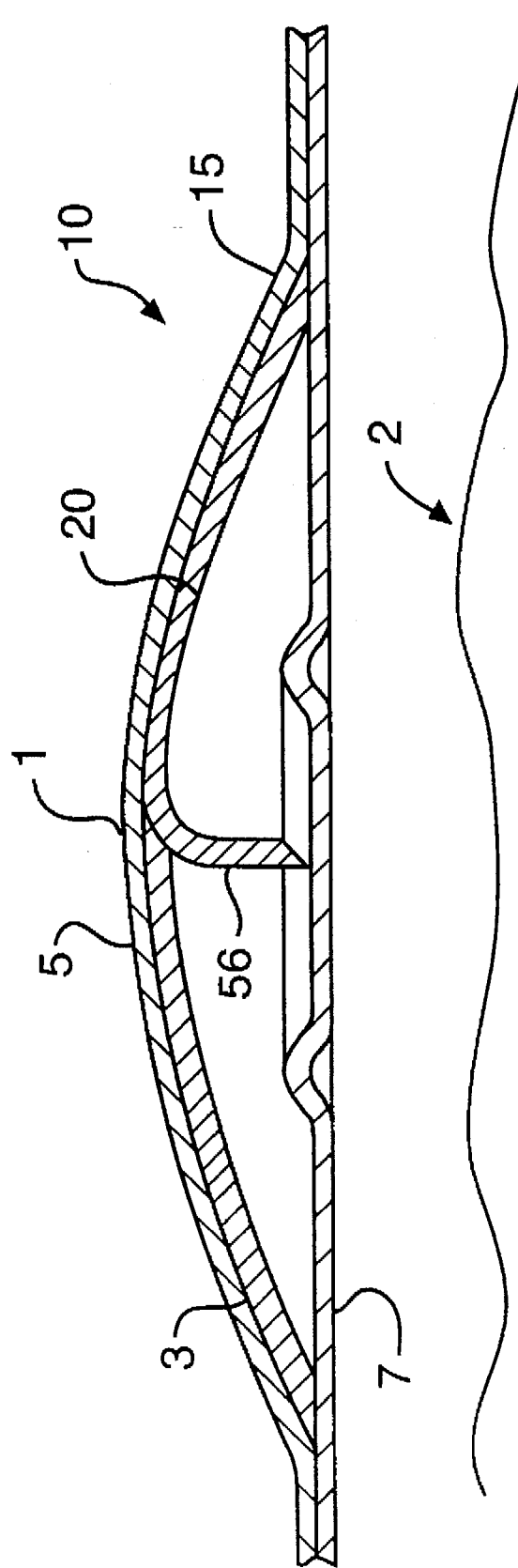
FIG. 1 is the liquid sampling and test apparatus in its simplest form. In this embodiment, the piercer is encapsulated between the conformal main body and the pierceable membrane.

FIG. 1 illustrates a preferred embodiment of the liquid sampling and test apparatus of the present invention. In this embodiment, a piercer disk 3 having a concave configuration is encapsulated within a housing 10 also comprising a main body 15 and a pierceable air impermeable membrane 7. The action of depressing a dome shaped head 5 of the main body 15 causes the protruding sharpened tip 56, which is integrally formed in the piercer disk 3, to pierce the pierceable membrane 7 and the epidermis 2, upon which it has been positioned for extraction of the sample. The deformed piercer shape, when it springs back to its dome shape, acts as a piston and draws the blood into the formed cavity on the concave side of the piercer disk 3.

Figure 2:
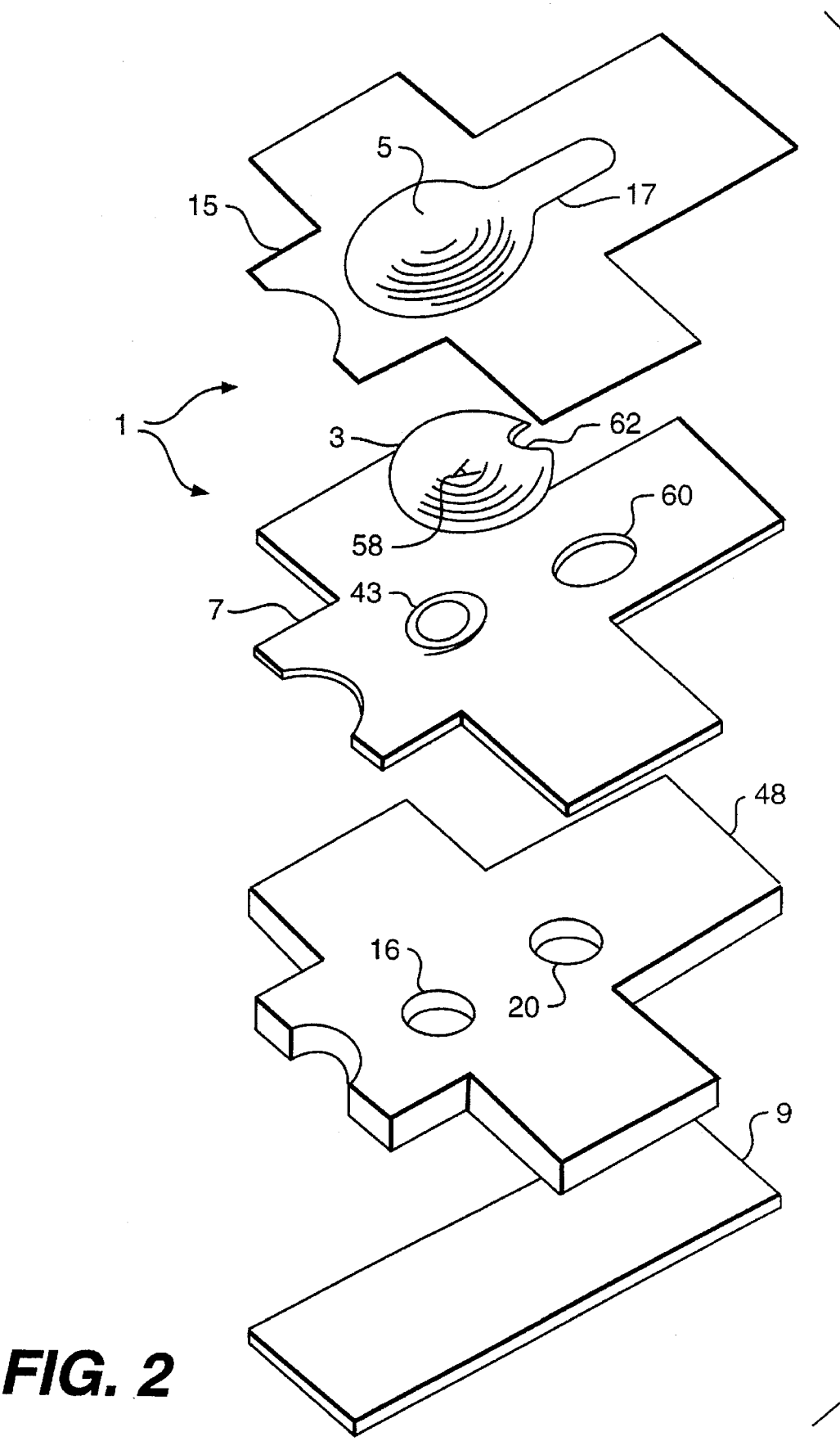
FIG. 2 is an exploded view of one preferred embodiment of the liquid sampling and test apparatus.

FIG. 2 is an exploded view of one preferred embodiment of the liquid sampling and test apparatus. The liquid sampling and test apparatus 1 is made of successive layers of elements bonded under an internally drawn vacuum, one layer on to the next, to form the assembly. The first layer from the bottom is a protective cover 9 attached to a main frame 48. This protective cover is removed prior to any use of the liquid sampling and test apparatus 1. The main frame 48 contains an inlet port 16 and a reservoir 20. A pierceable air impermeable membrane 7 is bonded to the upper surface of the main frame 48, sealing off an inlet port 16. The pierceable membrane may also contain a raised annular section 43 positioned above inlet port 16. A piercer disk 3 rests above the inlet port 16 and is held in that location by the main body 15, which bonds to the interfacing surface between the pierceable membrane 7 and the main body 15. The passageway 62 is oriented to be in line with a communicative passage 17. The liquid sampling and test apparatus 1 is placed on the area from which a liquid sample is to be taken.

In accordance with the present invention, the dome-shaped head 5 of the main body 15 is pressed downward, causing the piercer disk 3 to bend, thereby piercing the pierceable membrane 7, whereupon the liquid at the inlet port 16, under atmospheric pressure, fills the vacuum within an evacuated cavity 4 formed between the main body 15 and the pierceable membrane 7. The liquid then fills the communicative passage 17 and empties into the reservoir 20 through the access hole 60. This embodiment would best serve as an apparatus that would be submerged in the liquid to be sampled as the sample is then drawn.

Figure 3:
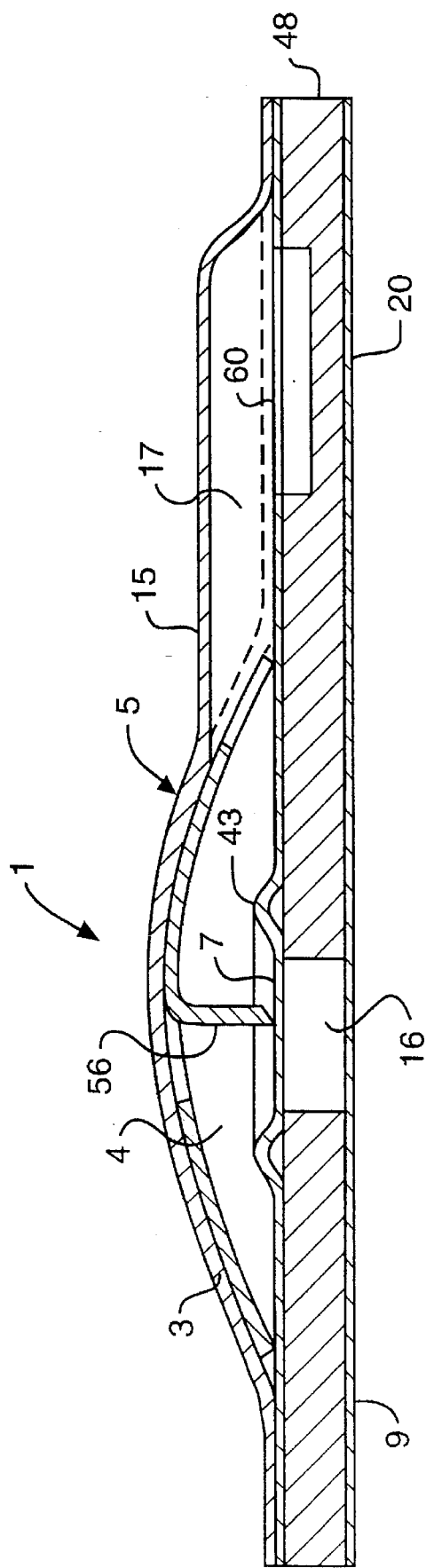
FIG. 3 is the cross-section of the assembled liquid sampling and test apparatus in FIG. 2.

FIG. 3 is the cross-section of the assembled liquid sampling and test apparatus 1. The main body 15 is made of any suitable material for creating the necessary shapes and having the necessary properties, for handling the samples. The piercer disk 3 inside the evacuatable cavity 4, when subjected to pressure applied to the dome shaped head 5 of the main body 15, bends and allows the protruding sharpened tip 56 of the piercer disk 3 to pierce the pierceable membrane 7. The liquid fills the entire evacuatable cavity 4, including the communicative passage 17 between the dome shaped head 5 and the reservoir 20, and passes through the access hole 60 and fills the reservoir 20.

Figure 4A:
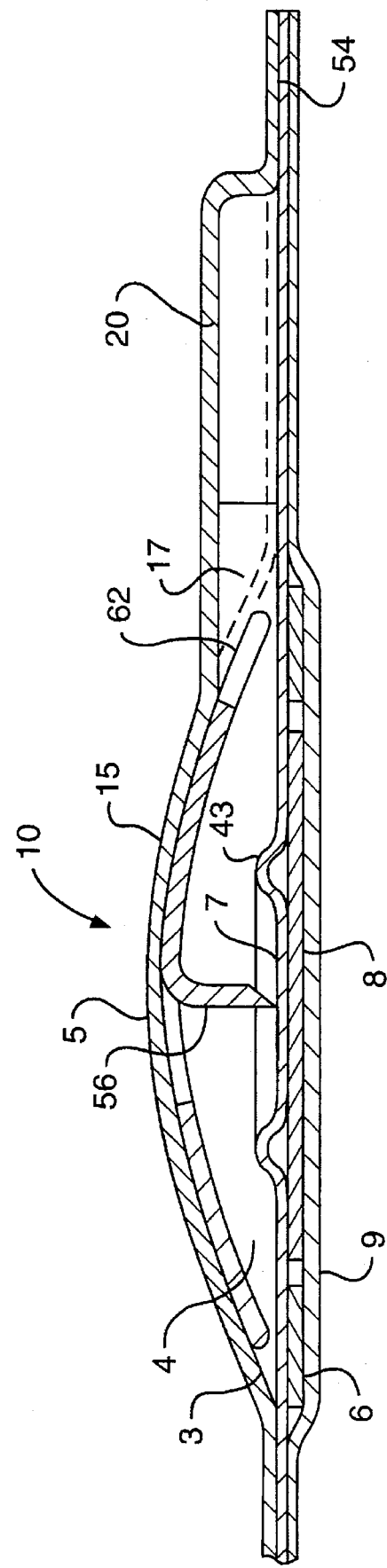
FIGS. 4a and 4b are cross-section and exploded views of the preferred embodiment for piercing the skin and drawing a blood sample from the pierced skin.
Figure 4B:
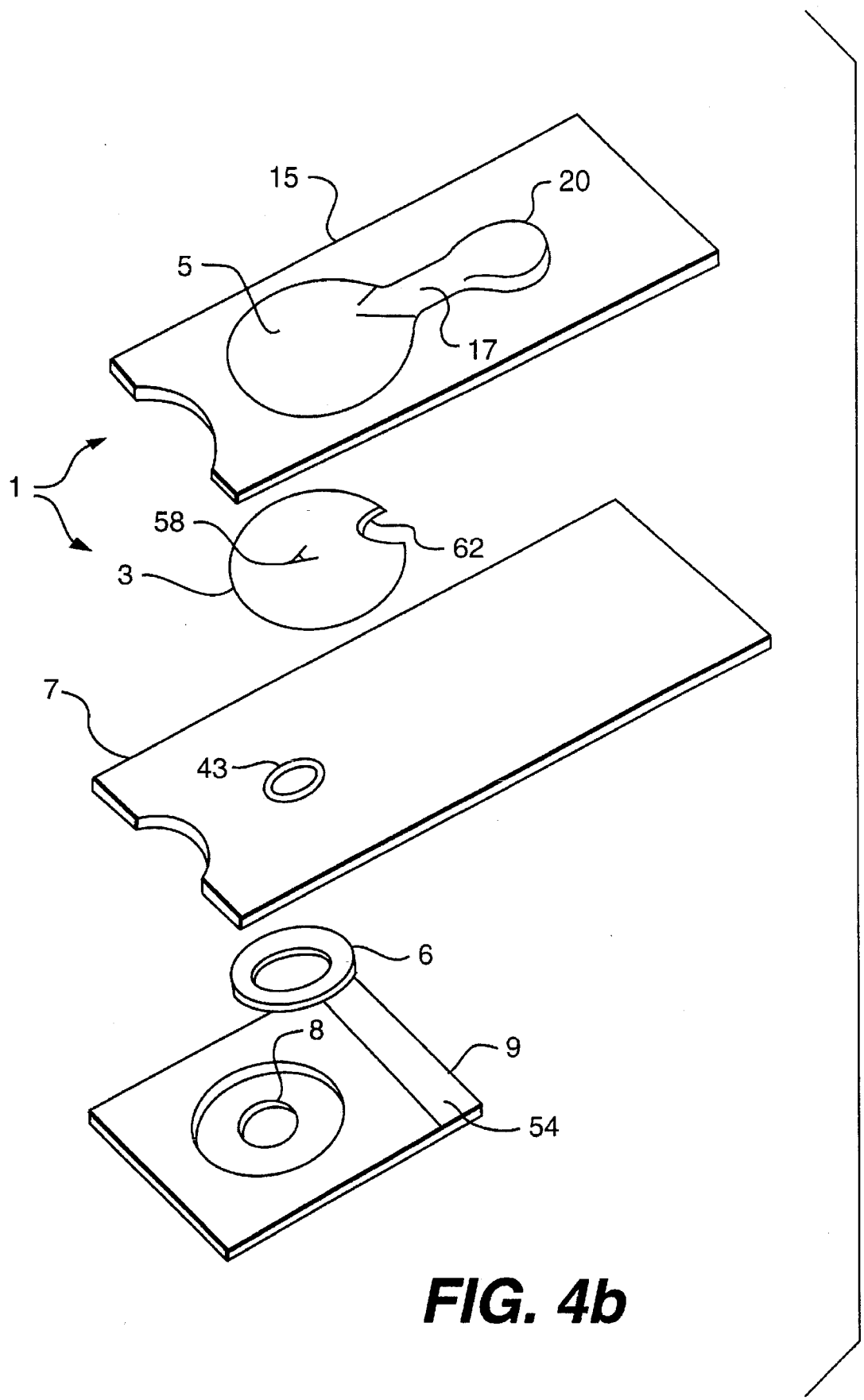

FIG. 4b provides an exploded view of the liquid sampler and test apparatus 1 shown in FIG. 4a, which is a preferred configuration for extracting samples of blood. This exploded view features one of many possible methods of fabricating the liquid sampling and test apparatus. The bottommost layer is protective cover 9, to which is permanently attached a non-pierceable disk 8. To minimize the risk of inadvertent contact with a needle, scalpel, or cannula point, the present invention utilizes a non-pierceable disk 8 as a part of the protective cover. The presence of the non-pierceable disk in the path of the piercer disk 3 effectively eliminates the potential for inadvertent pricking of the user.

The protective cover 9, is permanently secured to the pierceable air impermeable membrane 7 along a portion 54, and is adhesively connected to the pierceable membrane of the rest of its length, so that the cover 9 is peelable for most of its length.

The present invention also includes a sealing ring 6, which is permanently bonded to the same side of the pierceable membrane 7 as the protective cover 9. The sealing ring 6 is located on the pierceable membrane 7 in a position whereby the non-pierceable disk 8 nests concentrically with the sealing ring 6, and both are thereby protected and sealed by the protective cover 9. The sealing ring 6 also serves as a backing plate for the pressure from the piercer disk 3 when the pressure is applied to the dome-shaped head 5 to begin the liquid sampling process. The piercer disk 3 is oriented symmetrically over raised annular section 43 and is oriented to align passageway 62 with the communicative passage 17. The entire section is then bonded under a vacuum to the main body.

FIG. 4a shows the housing 10, which includes the main body 15, the evacuated chamber 4, the pierceable membrane 7, as well as the communicative passage 17 and the reservoir 20, which are integrally connected to the main body 15. The piercer disk 3 conforms to the inner surface of the dome-shaped head 5, in a manner which allows the protruding sharpened tip 56 to stand above the raised annular ring 43 of pierceable membrane 7. The main body 15 should be made of material appropriate for the tests to be conducted, since some materials tend to inhibit the blood coagulation time and others tend to enhance it.

There are times when it would be desirable to mix a reagent with the blood flowing into the reservoir 20. One means for accomplishing this is to coat the inside surface with a dissolvable coating of the reagent. When the blood fills the reservoir, the coating is dissolved and mixed with the reagent.

Figure 5:
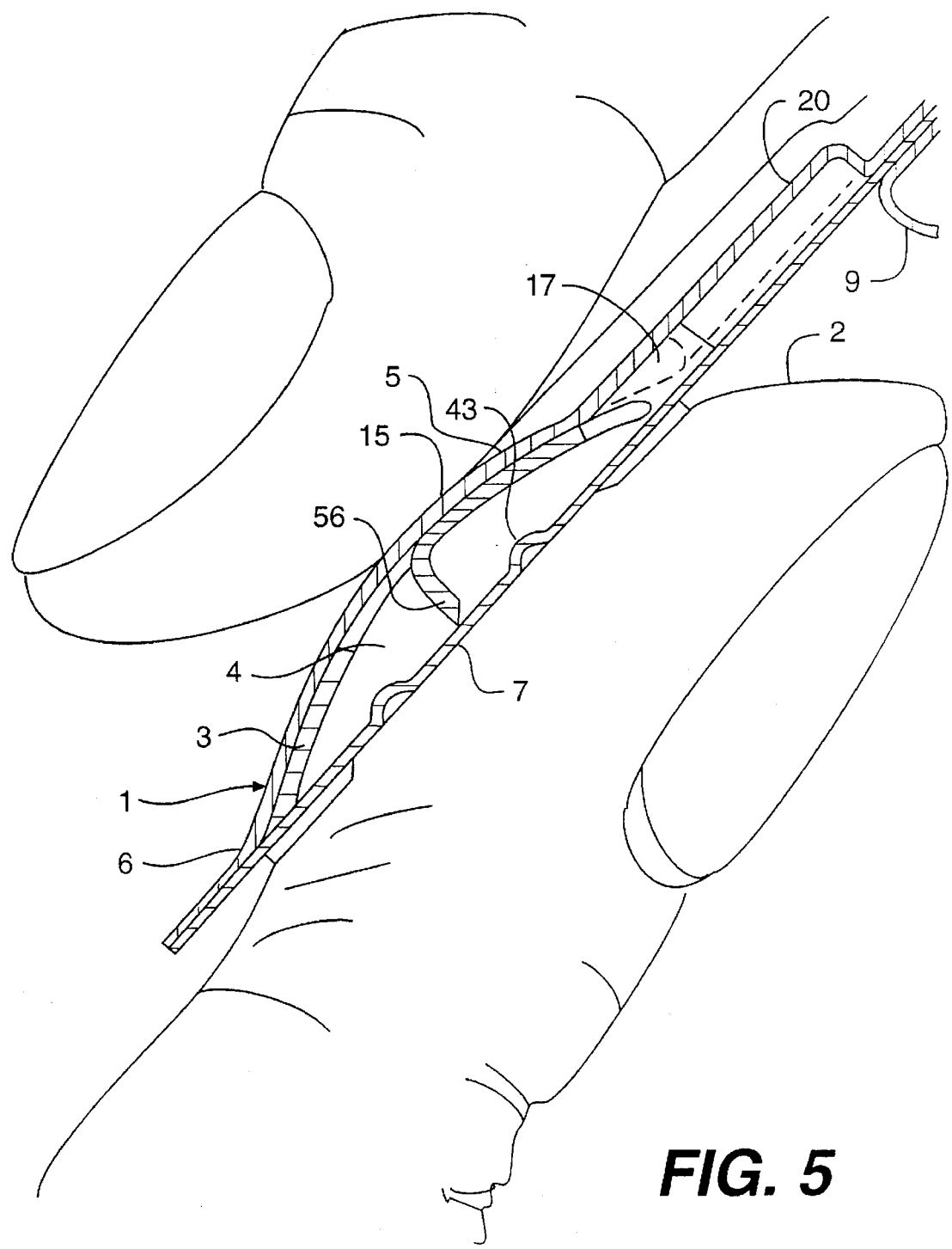
FIG. 5 depicts the method of using the embodiment in FIGS. 4a and 4b to draw a blood sample from the epidermis.

FIG. 5 depicts the method of using a blood sampling apparatus depicted in FIGS. 4a and 4b. Prior to use, the protective cover 9 is peeled back and remains in the peeled-back position during use. The main body 15 of the liquid sampling apparatus is pressed down against the area of the epidermis to be tested, such as the finger tip 2, thereby adhering the apparatus to the epidermis by the adhesive of sealing ring 6. By applying pressure, the dome-shaped head 5 of main body 15 is depressed, thereby causing the protruding tip 56 of piercer disk 3 to pierce the pierceable membrane 7. Liquid fills the entire evacuatable chamber 4 and fills into communicative passage 17 where it empties into reservoir 20.

Figure 6B:
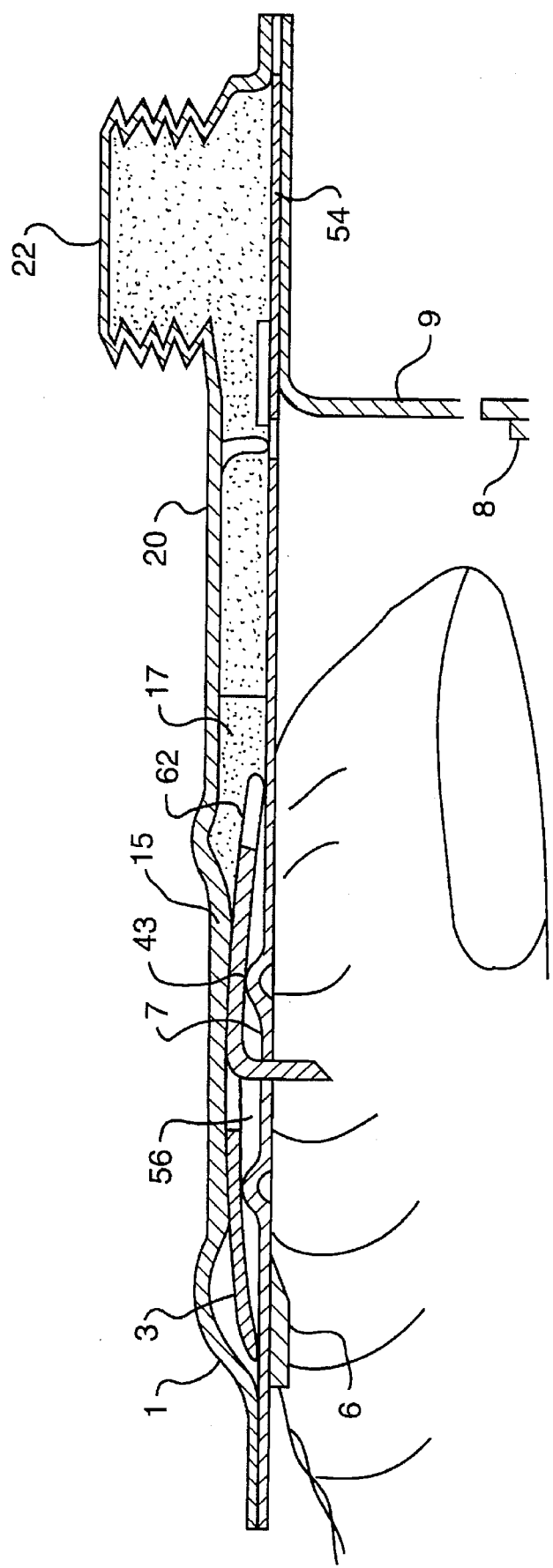

FIGS. 6a and 6b each is a cross section of the assembly of FIG. 4a with the added enhancement to the main body 15 of a capillary section 19 as an extension of the reservoir 20. This capillary section 19 connects to a bellows-like syringe 22, also integral in the material of the main body 15. When the liquid sampling and test apparatus is bonded under an internally-drawn vacuum, the bellows-like syringe 22, normally expanded as shown in FIG. 6b, is caused to collapse under the influence of the outside atmospheric pressure and the inside vacuum. The bellows-like syringe 22, is shown in its collapsed state in FIG. 6a. The sample collected in reservoir 20 could then ultimately be monitored using changes in its infrared transmissibility properties to detect blood coagulation time. The reservoir 20 could have many other shapes and still provide the functional characteristics required of the sample. It will be appreciated that a vacuum can be applied to the reservoir or chamber 20 by any number of conventional methods, including assembly of the apparatus under a vacuum.

Figure 7A:
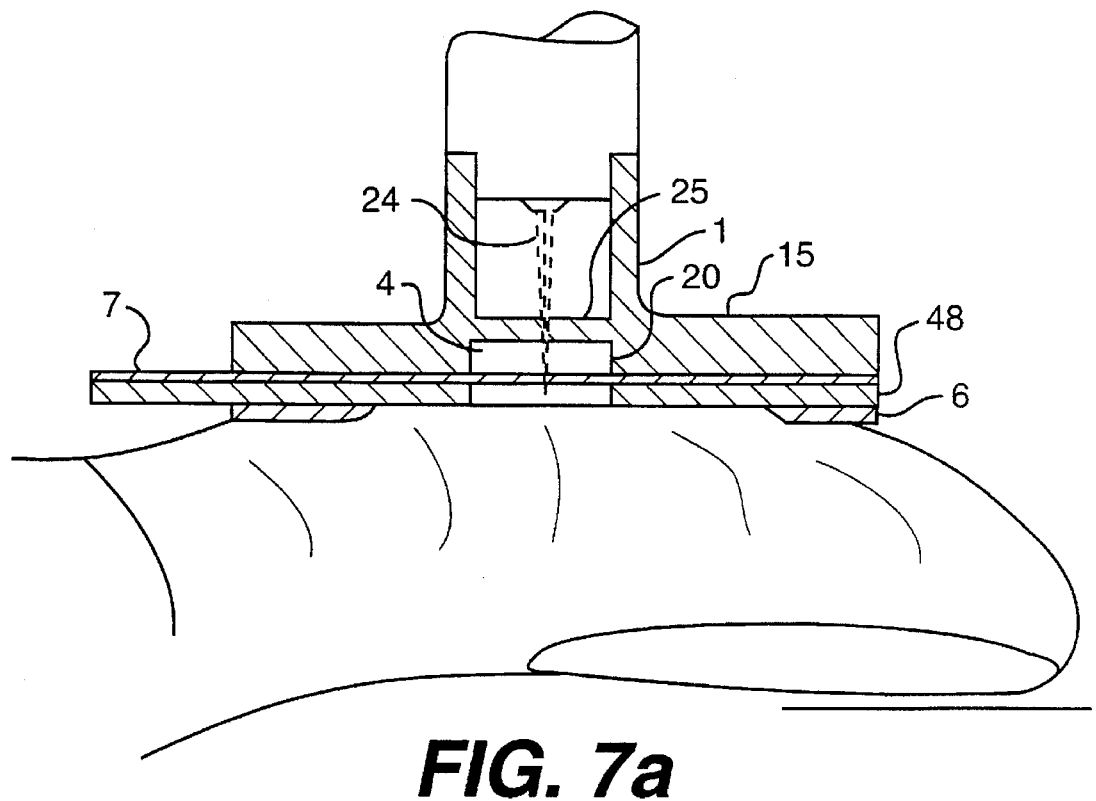
FIGS. 7a and 7b show an embodiment of the blood sampling and test apparatus where the piercer is a laser beam external to the apparatus. 7a shows the laser focused to pierce the pierceable membrane, and 7b shows the laser refocused to pierce the epidermis.
Figure 7B:
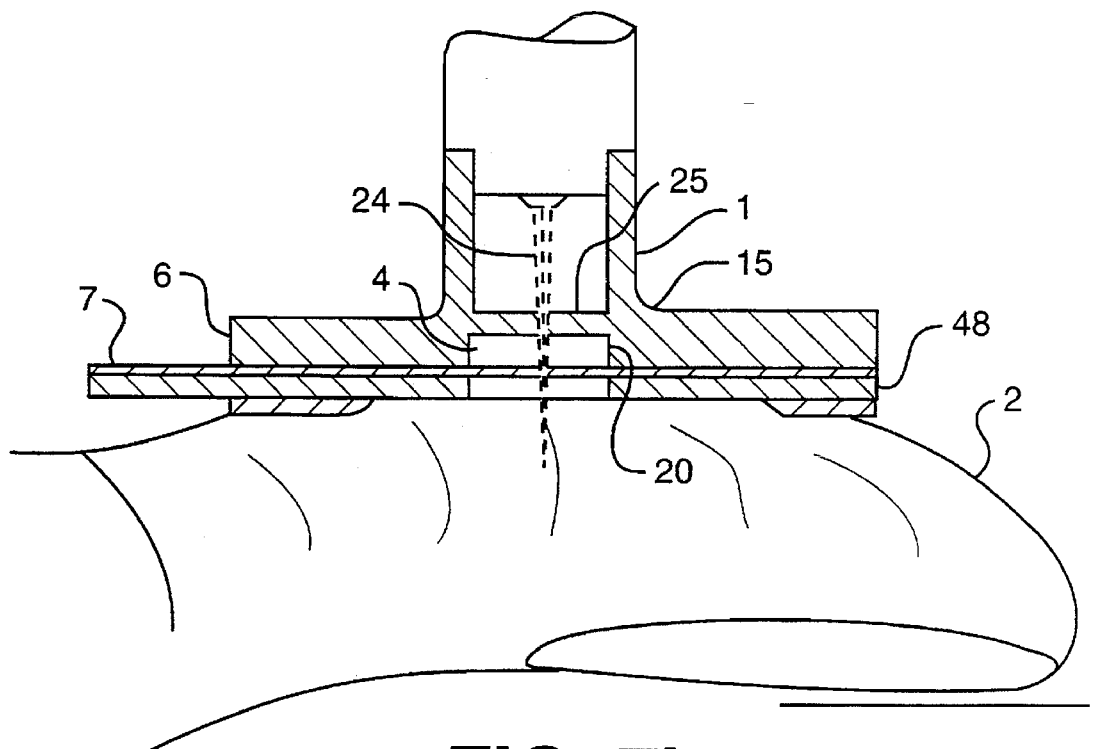

FIGS. 7a and 7b each; and shows an embodiment of the liquid sampling and test apparatus where the piercer is a laser beam 24 external to the apparatus. The housing 48 of the liquid sampling and test apparatus 1 is constructed with an aperture 25 through which a virtually unattenuated laser beam 24 can be passed in order to pierce the pierceable air impermeable membrane 7. Protective cover 9 has been peeled away to expose an adhesive ring 6. Once the pierceable membrane 7 is pierced, the sample is drawn into the sample reservoir 20. In this embodiment, the liquid sampling and test. apparatus has been constructed to have a vacuum drawn in the evacuatable cavity 4. As shown in FIG. 7a, the laser beam 24 is initially focused on to dissolve the material of the pierceable membrane 7. It is then refocused and directed to penetrate the epidermis 2, as shown in FIG. 7b. The blood then fills the evacuatable cavity 4.

Each of FIGS. 8a–8g shows possible implementation of the piercer disk 3, which preferably is formed of stainless steel. There are many conceivable shapes for the blade used to pierce pierceable membrane 7. According to the present invention, it has been found to be particularly advantageous to form the blade by shearing a section of the piercer disk 3 and bending the sheared section downward to provide the blade. The disk 3 itself is elastically deflectable, i.e., it returns to its original position, and therefore is responsive to depression of the housing 10.

Figure 8A:
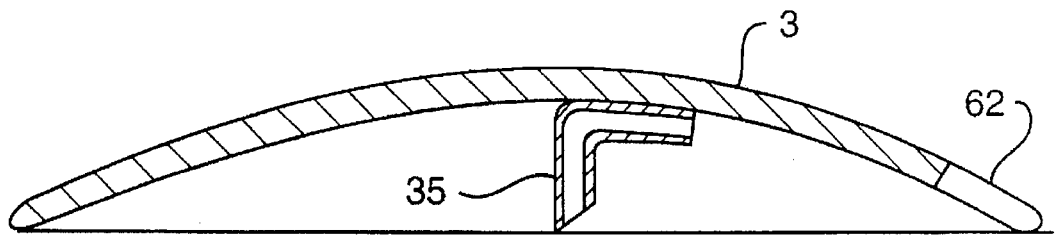
FIGS. 8a and 8b show several possible implementations of the piercer which provide special means for guiding the blood to enter the evacuatable cavity.

FIG. 8a shows a cannula 35, where the input end, which does the piercing, is sharpened at an angle and the output end is bent approximately at a right angle. This cannula 35 is permanently attached to the dome shaped head 5. The cannula 35 oriented in this fashion directs the flow of blood into the evacuatable cavity 4.

Figure 8B:
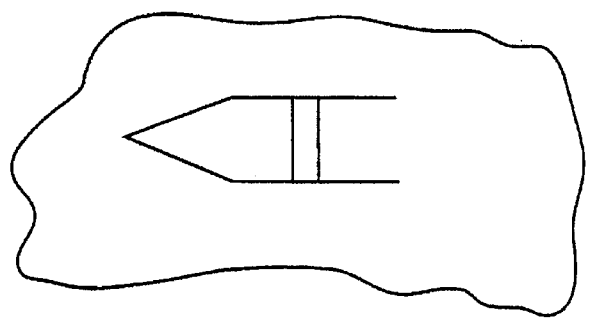
Figure 8C:
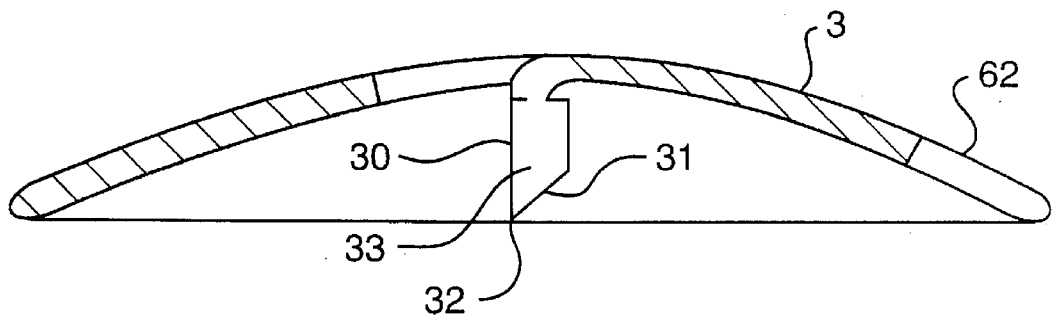

FIG. 8c shows the piercer disk 3 with its protruding sharpened tip 56 as a columnar "V"-shaped blade 30. This blade has been configured to provide lifting of the pierced section of the pierceable membrane 7 to maintain a wide open passage through the material. The leading edge 31 of the "V"-shaped blade 30 is cut at an angle with respect to the axis of the columnar section. Thus, the vertex 32 of the "V" section is in front of the tips of the side walls of the "V". The leading edge 31 is sharpened from the outside edges of the "V" toward the inside edges, making the cutting edge coincident with that inside edge. This edge is sharpened along the entire "V" to provide the cutting edge.

Figure 8D:
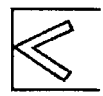

FIG. 8b is a top view of columnar "V"-shaped blade 30 of FIG. 8c. The dotted and bold lines indicate the configuration of the columnar "V"-shaped blade 30 as bent downward approximately at a right angle. FIG. 8d is a bottom view of the columnar "V"-shaped blade 30 of FIG. 8c, which illustrates its "V"-shaped configuration.

Figure 8E:
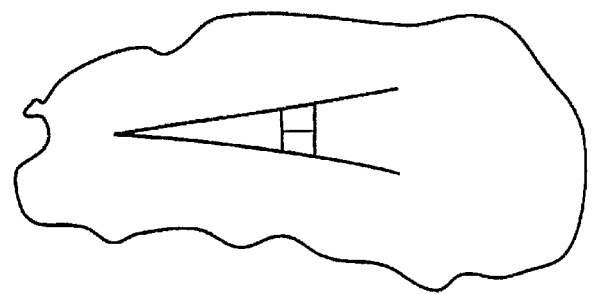
Figure 8F:
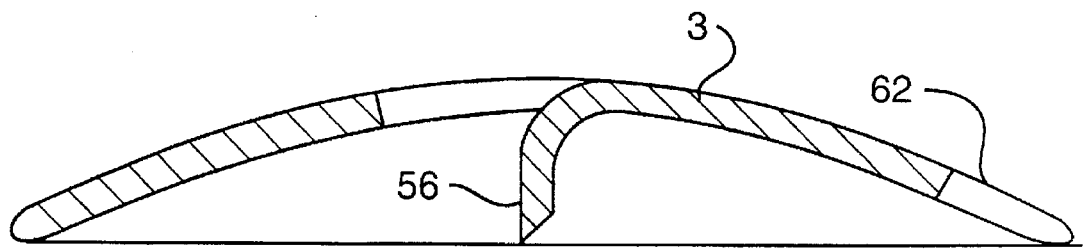

FIG. 8f depicts the preferred configuration of the blade as a protruding sharpened tip 56, integrally formed in the piercer disk 3. FIG. 8e is a top view of the protruding sharpened tip 56, bent downward toward the pierceable membrane 7.

Figure 8G:
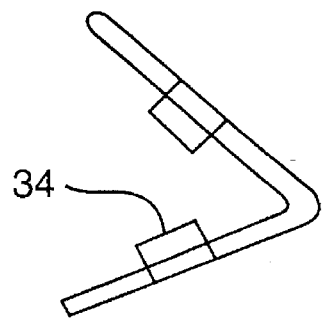

A section of the side walls of the "V"-section just above the sharpened edge and in close proximity of the vertex 32 of the "V" have "U"-shaped notches 33. The tab 34 created by the "U"-shaped notches 33 is bent toward the opposite walls of the "V" blade for a distance of at least the thickness of the "V" blade as shown in FIG. 8g. This protruding tab 34 is used to lift the "V"-shaped pierced section of the pierceable membrane 7 as the columnar blade 30 is retracted once piercing is complete.

Figure 9:
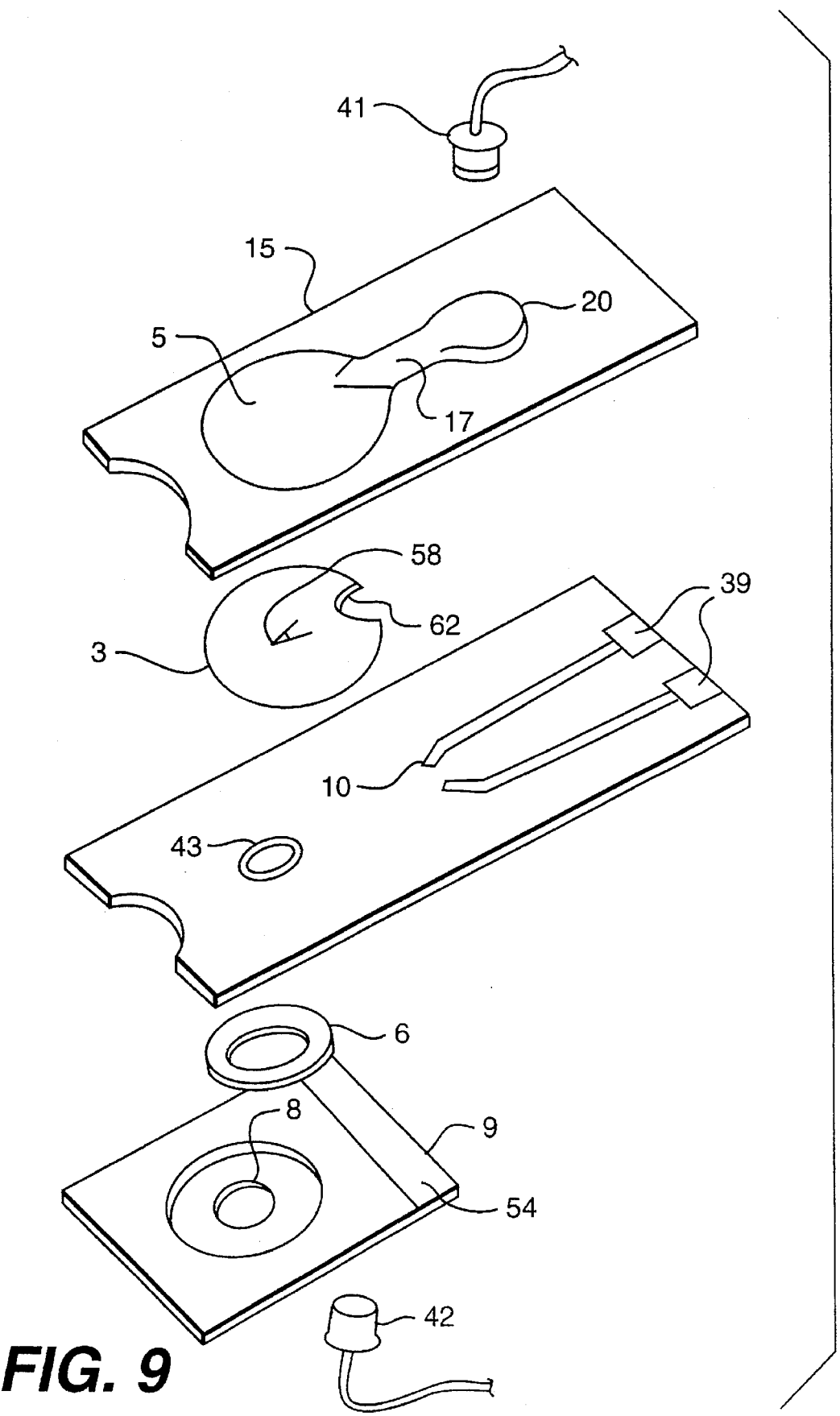
FIG. 9 shows the embodiment incorporating special electrical connections for initiating the timing of a test on the blood sample. It also shows the orientation of the infrared source and detectors, if they were used in the test.

FIG. 9 shows another embodiment useful for timing a test off a sample of a liquid, preferably blood. When the liquid sampling and test apparatus 1 is to be used in a timed test, such as blood coagulation timing, then the timing sequence could be initiated by the presence of the blood in the reservoir 20. According to the present invention, this is accomplished by having the blood bridge the gap between two electrical contacts 10. In one embodiment, the reservoir 20 has two spaced electrical contacts 10 emanating from two separate points within the reservoir 20. These contacts 10 continue as two leads 39, passing along the surface of pierceable membrane 7, through the sealed connection of the pierceable membrane 7 and the main body 15 to an externally accessible area, where they connect to control electronics. These control electronics measure the presence or lack of continuity between the two leads 39 resulting from the presence or lack of blood in the reservoir 20. This approach has been clinically demonstrated as a most effective approach. The inception of continuity initiates the countdown process for blood coagulation time determination.

Figure 10:
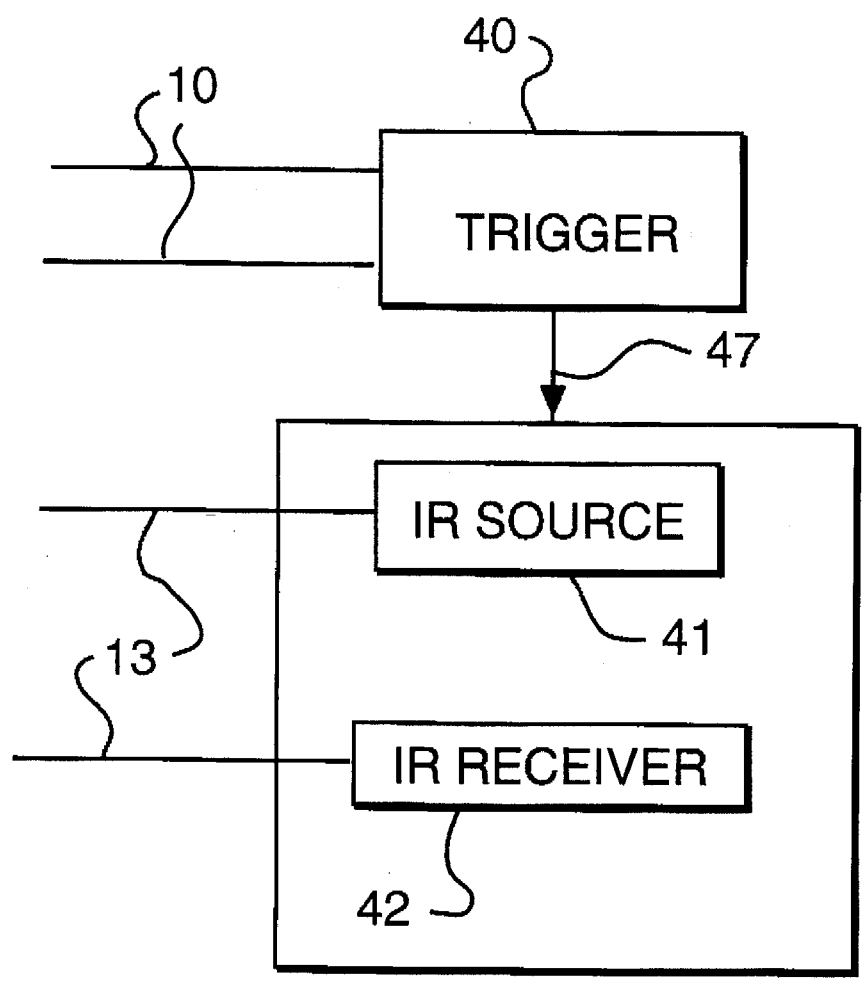
FIG. 10 shows a triggering circuit attached to electrical conductors for detecting presence of liquid which initiates infrared energy for testing the liquid in the sample reservoir.

As embodied herein and shown in FIG. 9, the present invention also includes an infrared source 41 and a detector 42 located above and below the reservoir 20, respectively. As shown in FIGS. 9 and 10, the infrared source 41 can radiate through the opening 58 created by the shearing and forming operation which was used to form the protruding sharpened tip 56 in the piercer disk 3. The infrared detector 42 can be positioned under the area of the pierceable membrane 7 in the vicinity of the pierced membrane. These elements may be used to determine the extent of blood coagulation, using conventional methods in the art.

As embodied herein and shown in FIG. 10, the present invention includes a triggering circuit 40 attached to electrical conductors 10 via the two leads 39. Upon detection of the liquid by the triggering circuit 40, a signal 47 is sent to the infrared source 41 to turn on the infrared energy. In the case of blood coagulation time measurement, the energy is directed across the pool of blood in the reservoir 20. It will be appreciated that the reservoir 20 can be shapes other than the circular shape shown in the drawings and still have the same utility.

Figure 11:
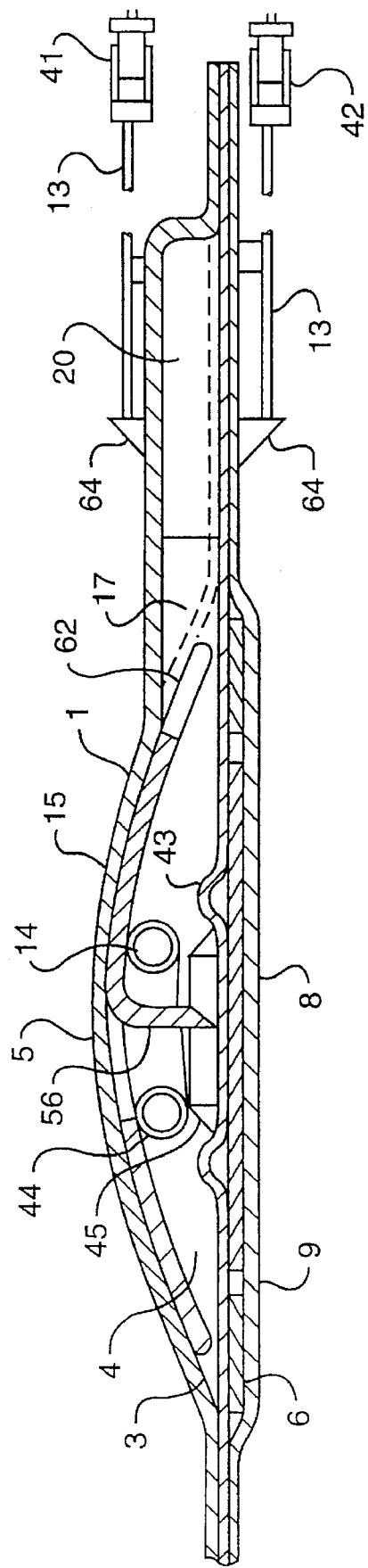
FIG. 11 shows the use of a frangible container containing a substance to be mixed with the blood sample drawn into the apparatus.

FIG. 11 shows an embodiment of the liquid sampling and test apparatus 1 where it is desired to mix a reagent 14 with the incoming blood. One technique for accomplishing this is to place a frangible container 44 having the reagent 14 sealed inside its walls, in the evacuatable cavity 4. For example, heparin, an anticoagulant, could serve as the reagent to determine its effects on coagulation of a blood sample. The frangible container 44 is bonded to the concave surface of the piercer disk 3 so that it surrounds the protruding sharpened tip 56. An annular protruding fracturing cylinder 45 is positioned directly below it and is attached to the pierceable membrane 7. When the piercer disk 3 is pressed to pierce the pierceable membrane 7, the frangible container 44 is fractured by the annular protruding fracturing cylinder 45, thereby releasing the reagent 14, which mixes with incoming blood.

The infrared source 41 and detector 42 can be located remote from the reservoir 20 and a fiber optic guide means 13 can be attached to the liquid sampling and test apparatus 1 to direct the infrared energy through the blood sample in the reservoir 20. This accomplishes the blood coagulation timing measurement, as described above.

In all of the embodiments the piercer disk 3 is encapsulated in a sterile container until it is used and then it retracts into that same container for disposal. During storage of the unit, the non-pierceable disk 8 on the inside surface of the protective cover 9 protects the user from an inadvertent pricking by the piercer disk 3.

While the invention has been described in terms of preferred embodiments in a specific system environment, those skilled in the art recognize that the invention can be practiced with modifications, in other and different hardware and software environments with the spirit and scope of the appended claims.

What is claimed is:

1. An apparatus for sampling liquid from an object comprising:

a deformable housing defining an evacuated chamber adapted to receive a liquid, said housing having a pierceable, air impermeable membrane;

a resilient piercer member abutting along a wall of said chamber and adapted to puncture said membrane;

whereby depression of said housing proximate said piercer member urges said piercer member to puncture said membrane, thereby forming an opening, so that liquid is drawn through said opening and into said chamber as said piercer member returns to said housing.

2. The apparatus as defined in claim 1, also including a seal member disposed outside of said chamber and attached to said membrane portion for applying a seal between said housing and the object when said layer is removed.

3. The apparatus as defined in claim 1, wherein said housing includes a dome-shaped head, and wherein said piercer member includes a first portion conforming substantially to said dome-shaped head and a second portion extending substantially orthogonally relative to said first portion.

4. The apparatus as defined in claim 3, wherein said second portion includes a blade for piercing said pierceable membrane into a section having a shape corresponding to said blade.

5. The apparatus as defined in claim 4, wherein said second portion includes a tab substantially adjacent said blade for urging said section toward said chamber when said piercer member returns to said housing.

6. The apparatus as defined in claim 4, wherein said blade has a v-shaped cross-section.

7. An apparatus for sampling blood from an epidermis comprising:

a deformable housing defining an evacuated chamber adapted to receive blood, said housing having a pierceable, air impermeable membrane; and a resilient piercer member adjacent a wall of said chamber and adapted to puncture said membrane;

whereby depression of said housing proximate said piercer member causes said piercer member to puncture said membrane, thereby forming an opening along said membrane and urging said piercer member into engagement with the epidermis, so that blood is drawn from the epidermis, through said opening, and into said chamber, as said piercer returns to said housing.

8. The apparatus as defined in claim 7, also including a seal member disposed outside of said chamber and attached to said portion of said membrane for applying a seal between said housing and the epidermis when said layer is removed.

9. The apparatus as defined in claim 7, wherein said housing includes a pair of spaced electrical contacts for detecting the presence of blood therebetween.

10. The apparatus as defined in claim 9, also including an infrared sensor electrically connected to said contacts for measuring coagulation of the blood within said chambers.

11. The apparatus as defined in claim 7, also including a frangible member containing a reagent, said frangible member being disposed within said chamber and aligned with said piercer member, whereby said piercer member is adapted to fracture said frangible member so that said reagent mixes with the blood within said chamber.

12. The apparatus as defined in claim 7, wherein said removable layer is non-pierceable.

13. The apparatus as defined in claim 7, wherein said housing includes bellows for increasing the flow of blood into said chamber.

14. An apparatus for sampling liquid from an object comprising:

a deformable housing defining an evacuated chamber adapted to receive a liquid, said housing having a pierceable, air impermeable membrane; and a piercer adapted so that actuating the piercer causes said piercer to puncture said membrane and penetrate the object, thereby forming an opening, so that liquid is drawn from the object through said opening and into said chamber, and said piercer is adapted to be de-actuated so that said membrane is no longer pierced and said object is no longer penetrated.

15. The apparatus of claim 14, wherein said piercer is a resiliently mounted blade abutting along a wall of said housing.

16. The apparatus of claim 1, further comprising a removable layer covering at least a portion of said membrane.

17. The apparatus of claim 7, further comprising a removable layer covering at least a portion of said membrane.

* * * * *